(12) United States Patent
Herdeis et al.

(10) Patent No.: US 7,820,651 B2
(45) Date of Patent: Oct. 26, 2010

(54) PREPARATION OF ANTIMICROBIAL FORMULATIONS USING 7-OXA-2-THIA-1,5-DIAZABICYCLO[3.3.1] NONANE-2,2-DIONE

(76) Inventors: Claus Herdeis, Strassbergerstrasse 18, 80809 München (DE); Christian Edwin Weis, Jagerstrasse 5a, 97297 Waldbüttelbrunn (DE)

( * ) Notice: Subject to any disclaimer, the term of this patent is extended or adjusted under 35 U.S.C. 154(b) by 701 days.

(21) Appl. No.: 11/672,613

(22) Filed: Feb. 8, 2007

(65) Prior Publication Data
US 2008/0027043 A1  Jan. 31, 2008

(30) Foreign Application Priority Data
Jul. 25, 2006  (EP) .................. 06015520

(51) Int. Cl.
*A61K 31/54* (2006.01)
*A61K 9/00* (2006.01)
*C07D 513/00* (2006.01)

(52) U.S. Cl. .................. 514/222.8; 424/400; 544/48
(58) Field of Classification Search .............. 514/222.8; 424/400; 544/48
See application file for complete search history.

(56) References Cited

FOREIGN PATENT DOCUMENTS

| CH | 482 713 | 1/1970 |
|---|---|---|
| EP | 0863133 B1 | 9/2001 |
| EP | 1089738 B1 | 5/2006 |
| WO | WO 98/28027 | 7/1998 |
| WO | WO 00/01391 | 1/2000 |

OTHER PUBLICATIONS

B. Jurewitsch et al.: Taurolidine lock: the key to prevention of recurrent catheter-related bloodstream infections, in: Clinical Nutrition, vol. 24, No. 3, Jun. 2005.
Alan R. Kennedy, et al.: Two new compounds by reaction of taurolidine with methylene glycol, in: Acta Crystallographica Section C, 1999, pp. 232-234.
M.M. Mughal: Complications of intravenous feeding catheters, in: British Journal of Surgery, vol. 76, No. 1, Jan. 1989.
Muntzer Mughal et al.: "Infected Feeding Lines", in: Care of the critically ill, vol. 6, No. 6, Nov./Dec. 1990.
B. Jurewitsch, et al.: Taurolidine 2% as an antimicrobial lock solution for prevention of recurrent catheter-related bloodstream infections, in: Journal of Parenteral and Enteral Nutrition, vol. 22, No. 4, Jan. 1998.

*Primary Examiner*—Sreeni Padmanabhan
*Assistant Examiner*—Kendra D Carter
(74) *Attorney, Agent, or Firm*—Henry M. Feiereisen; Ursula B. Day

(57) ABSTRACT

Use of 7-oxa-2-thia-1,5-diazabicyclo[3.3.1]nonane-2,2-dione ("cyclotaurolidin") for the preparation of antimicrobial formulations, in particular antimicrobial solutions for technical or medical purposes and of aqueous lock solutions for catheters and port systems for preventing infections and sepsis of patients.

14 Claims, No Drawings

PREPARATION OF ANTIMICROBIAL FORMULATIONS USING 7-OXA-2-THIA-1,5-DIAZABICYCLO[3.3.1] NONANE-2,2-DIONE

CROSS-REFERENCES TO RELATED APPLICATIONS

This application claims the priority of European Patent Application Serial No. 06015520.7 filed Jul. 25, 2006, pursuant to 35 U.S.C. 119(a)-(d), the subject matter of which is incorporated herein by reference.

BACKGROUND OF THE INVENTION

The present invention relates to the field of antimicrobial (antiseptic or microbicidal) formulations for medical and other purposes, the formulations being in particular aqueous solutions which contain an active substance with antimicrobial and antiendotoxic activity as explained by an irreversible N-methylol group transfer to the microbial cell wall and endotoxins.

Substantially the compound taurolidin may be mentioned as the active substance whose activity is interpreted in terms of said methylol group transfer. Taurolidin is a substance which can be structurally derived from the aminosulfonic acid taurine. Taurolidin has the structural formula (I) and, in aqueous solution, is in equilibrium with taurultam (II) and methylol taurultam (III).

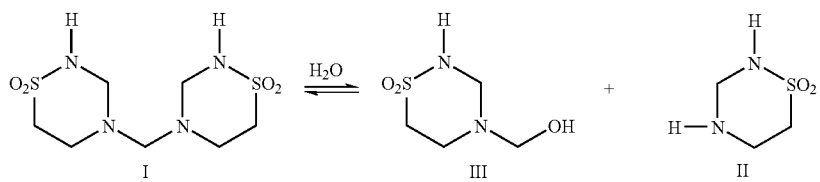

The preparation of taurolidin was first described in the Swiss patent application CH 482713 A. Taurolidin is prepared by reacting taurinamide(2-aminoethanesulfonamide) with 1.5 equivalents of formaldehyde or its hydration product methylene glycol $CH_2(OH)_2$ formed in aqueous solution. The known process was considerably improved by an improved process for the preparation of taurinamide according to EP 0 863 133 B1.

The formation of taurolidin from taurinamide and formaldehyde can be described as a condensation process in which 2 equivalents of taurinamide and 3 equivalents of formaldehyde participate, which gives a ratio of taurinamide to formaldehyde of 1:1.5 for the overall compound taurolidin. The hydrolytic cleavage of taurolidin according to the above equation results in the formation of the compounds methylol taurultam and taurultam, which, considered individually, may be regarded as condensates of taurinamide with 2 equivalents or 1 equivalent, respectively, of formaldehyde.

Taurolidin has long been commercially available in the form of aqueous solutions under the trade name Taurolin®, in particular as Taurolin 2% instillation solution having a content of 2.0 g of taurolidin and 5.0 g of polyvinylpyrrolidone per 100 ml of water, and as Taurolin® Ringer 0.5% surgical irrigation solution with 0.50 g taurolidin, 1.25 g of polyvinylpyrrolidone and a mixture of inorganic salts per 100 ml of water.

The medical uses of Taurolin® solutions are based substantially on the antimicrobial and antiendotoxic activity of taurolidin. The 0.5% Taurolin solution serves in particular for the intraoperative irrigation of the abdominal cavity, while applications by instillation via drains are stated for 2% Taurolin solutions in particular in diffuse purulent peritonitis and perforative appendicitis. Other applications stated by the manufacturer are prophylaxis in the case of soft tissue and bone injuries and for thoracic empyema. In various patent applications and scientific publications, further potential uses of Taurolin®, for example in dental medicine and oral hygiene, in tumor diseases and in dermatology, are described, and the effect on a large number of physiological parameters by local or parenteral administration of Taurolin® solutions or taurolidin solutions was investigated.

It has furthermore already been known since 1989 that the known Taurolin® solutions can also be used for controlling so-called "catheter sepsis" (cf. Mughal, Br. J. Sur. (1989) 76(1), pages 15 to 21; cf. also J. of the Critically Ill (1990) 6(6), pages 228 to 231). "Catheter sepsis" is one of the terms for severe complications which may occur in persons in whom catheters are implanted for repeated supply of medicaments or nutrient solutions or for hemodialysis purposes. As "catheters" may also be regarded the so-called port systems which are likewise permanently implanted and provide external access to central blood vessels of a patient. If, during the use of the permanently applied catheters or port systems, these catheters or port systems become populated with pathogenic bacteria, for example through a formation of biofilms on the inner walls of the catheters or port systems or the associated pathways, such as, for example, hollow needles, the patient may suffer dangerous local and in particular systemic infections (sepsis).

It has therefore long been known in principle to fill catheters and port systems with antimicrobial solutions which prevent colonization of the catheters and port systems by microorganisms and the formation of biofilms controllable only with difficulty with antibiotics or antiseptic agents, during those periods when, for example, no medicaments or nutrient solutions are supplied or no blood is taken.

European Patent application EP 0 946 221 A1 describes the use of a Taurolin® solution as a lock solution, it being intended that the lock solution be washed into the blood stream before resumption of operation of the catheter with a salt solution. Since the lock solution enters the patient's body in such a procedure, the lock solution must fulfill all preconditions which are set for medicaments to be administered parenterally.

While EP 0 946 221 A1 substantially describes the use of the customary 2% by weight Taurolin® solutions which contain polyvinylpyrrolidone in addition to taurolidin, European Patent EP 1 089 738 B1 discloses a use of taurolidin for lock solutions in modified form, in particular as a solution of taurolidin in a buffer system comprising trisodium citrate and citric acid. The buffer system serves for optimizing the solubility of the taurolidin and its antibacterial activity, in addition the anticoagulation properties of citrate being utilized for preventing blocking of the catheter exits by clots which can be formed from blood. Lock solutions of the type described in EP 1 089 738 B1 are today as a rule no longer washed into the circulation but sucked out of the catheter or port system before it is put into operation again. This has, inter alia, the advantage that the lock solutions do not enter the patient's body and are therefore not regarded as therapeutic agents, which have to meet strict registration requirements for therapeutic agents but as disinfectants or antiseptic agents acting only externally.

Although, for example in comparison with solutions of antibiotics, the use of taurolidin in lock solutions, in particular in lock solutions with added citrate, leads to a decisive improvement with regard to the control of infections which are caused by microbial contamination of catheters and port systems, improvements are still possible in said area. Although taurolidin solutions are effective against an extremely broad spectrum of bacteria (prokaryotic microorganisms), its efficacy against eukaryotic microorganisms (fungi; e.g. yeasts or molds) is limited.

Owing to the limited solubility of taurolidin in aqueous media, the activity of taurolidin-based aqueous antimicrobial solution cannot be arbitrarily increased by concentration increases. This observation relates not only to lock solutions but generally to taurolidin-based microbicidal (antimicrobial; antiseptic) aqueous solutions, also for other known or conceivable intended uses.

SUMMARY OF THE INVENTION

According to one object of the present invention a method for the production of an antimicrobial formulation is disclosed for use in a technical or medical application, comprising the steps of: dissolving or dispersing an antimicrobial amount of 7-oxa-2-thia-1,5-diazabicyclo[3.3.1]nonane-2,2-dione ("cyclotaurolidine") in a suitable carrier for a preparation of an antimicrobial formulation.

According to a further aspect of the present invention a method for producing 7-oxa-2-thia-1,5-diazabicyclo[3.3.1]nonane-2,2-dione ("cyclotaurolidine") comprises the steps of adding a solution of 2-aminoethanesulfonylamide(taurinamide) to an aqueous solution of formaldehyde containing formaldehyde in at least 3 times the stoichiometric amount based on the amount of taurinamide to obtain a reaction solution; therafter cooling the reaction solution to obtain a solid reaction product, filtering the solid reaction product off from the reaction solution and, optionally purifying the reaction product by recrystallization.

The novel preparation of formulations having antimicrobial activity which is based on a methylol group transfer from the species present in the formulation to microorganisms, which preparation makes it possible, in said context, to provide effective formulations whose efficacy with respect to microorganisms, in particular with respect to eukaryotic microorganisms, is increased in comparison with known taurolidin solutions, but which simultaneously makes it possible to modify the desired activity and, for example, to adapt it completely to the taurolidin solutions known to date, in particular taurolidin lock solutions, if higher activity is not required or is to be avoided in the specific case owing to undesired side effects.

According to certain embodiments of the present invention, this object is achieved by using not taurolidin but the compound 7-oxa-2-thia-1,5-diazabicyclo[3.3.1]nonane-2,2-dione, which is referred to in the further application simply as "cyclotaurolidine", for the preparation of the antimicrobial formulations.

According to another aspect of the present invention a method of preventing infections and sepsis in parients is disclosed which comprises steps of applying the antimicrobial formulation as a lock solution to catheters and port systems used on a patient for preventing infections and sepsis in patients caused by microbial contamination, by filling the respective cathertor or port system during medical non-use with the antimicrobial formulation of cyclotaurolidine.

The present invention therefore relates in general to the use of cyclotaurolidine for the preparation of antimicrobial (microbicidal) or antiseptic formulations for any desired purpose. In addition to uses for medical purposes, in particular uses as aqueous lock solutions, these purposes also include uses for other technical purposes, for example in agents for surface sterilization of body parts or objects which should have sterile surfaces, for example of contact lenses, implants, (e.g. stents) and other instruments which are used in such a way that they may cause infections. Said use can also be formulated as a novel process for the preparation of solutions starting from the novel starting product cyclotaurolidine.

The formulations may be not only solutions but also gels and ointments in vehicles optimized for the respective intended use.

The invention furthermore relates to the solutions themselves obtained on using cyclotaurolidine for the preparation of aqueous solution, in particular of the development as lock solutions for catheters and port systems and to the use of such solutions prepared from cyclotaurolidine as lock solutions in catheters and port systems. Thus, the invention also refers to an aqueous lock solution for catheters and port systems with cyclotaurolidine and monosodium citrate in aqueous solution, the lock solution having a pH in the range of from 4.5 to 7.5, preferably of a pH from 5.5 to 7.5.

The invention furthermore relates to a novel process which was developed by the inventors and permits the preparation of cyclotaurolidine in a simple manner in high yields.

The compound designated herein as cyclotaurolidine is known per se. In the publication by Alan R. Kennedy et al. "Two new compounds by reaction of taurolidin with methylene glycol", Acta Cryst. (1999). C55, 232-234, it is stated that this compound is obtained if taurolidin is reacted with an excess of methylene glycol (aqueous formaldehyde). Said compound has the structural formula (IV):

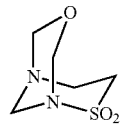

IV

Structurally, this compound may be regarded as taurultam whose two ring nitrogen atoms are linked by a dimethylene ether bridge with formation of a bicyclic structure. The compound may also be regarded as the product of a condensation reaction of taurinamide with 3 equivalents of methylene glycol or formaldehyde. 1 equivalent of methylene glycol forms the $CH_2$ group which is also present in taurultam. The oxygen-containing bridge is formed from two further taurultam-N-bonded methylene glycol units in a subsequent condensation reaction.

Said compounds were striking as a slightly soluble byproduct which crystallizes out in an undesired manner from taurolidin solutions under certain conditions. Since it was obtained by reaction of taurolidin, which is valuable as an active substance, with further methylene glycol or formaldehyde, its targeted preparation was not likely to have appeared attractive to date especially since the compound is more lipophilic than taurolidin. Furthermore, there were no known data at all on the antimicrobial activity of the compound.

However, investigations by the inventors of the present application into the solubility and antimicrobial activity of cyclotaurolidine have now led to the surprising result that, in spite of the higher lipophilicity of the compound, aqueous solutions of cyclotaurolidine not only are equivalent to the customary more highly concentrated taurolidin solutions with regard to their antimicrobial activity against prokaryotic microorganisms (bacteria), but that the aqueous solutions of cyclotaurolidine are also substantially more effective against problematic eukaryotic microorganisms (yeasts, molds) than more highly concentrated aqueous solutions which were prepared by dissolving taurolidin.

In aqueous solutions of cyclotaurolidine, an active substance is present, optionally also in the form of its hydrolytically formed equilibrium products, in which the molar ratio of structural units which are derived from taurinamide to structural units which are derived from methylene glycol or formaldehyde (methylene groups between ring nitrogen atoms or between nitrogen and oxygen atoms) is 1:3, whereas the corresponding ratio in solutions which were prepared using taurolidin is 1:1.5. This finding can serve as an explanation as to why solutions of cyclotaurolidine which are only half as concentrated as or even less concentrated than taurolidin solutions have at least comparable antimicrobial activities.

Compared with solutions of taurolidin, antimicrobial aqueous solutions prepared by dissolving cyclotaurolidine therefore have various advantages which are important, for example, for applications in which higher efficacy against eukaryotic microorganisms (yeasts, molds) is required than that of the customary taurolidin solutions. Such a potential application comprises, for example, a fungicidal solution for medical or hygiene purposes, for example for the treatment of the skin surface. Applications as preservatives for technical, cosmetic and food purposes also appear possible.

In cases where increased activity of the aqueous solutions prepared using cyclotaurolidine is not required or the higher reactivity gives rise to reservations in the respective use, the activity of the aqueous cyclotaurolidine solutions can be changed by adding taurinamide or taurinamide hydrochloride in a tailor-made manner. By addition of taurinamide, the ratio of methylene groups from methylene glycol/formaldehyde to taurinamide can be continuously shifted. As a result, modification of the antimicrobial activity of the aqueous solutions and also the solubility of the proportions of the active substance or of its equilibrium hydrolysis products which are present in the aqueous solution is possible. If taurinamide or taurinamide hydrochloride is added to the cyclotaurolidine solution in an amount such that the ratio of methylene groups which are derived from methylene glycol to taurinamide is reduced from the ratio 3:1, as present in cyclotaurolidine, to 1.5:1, as present in taurolidin solutions (addition of 1 equivalent of taurinamide per equivalent of cyclotaurolidine), the antimicrobial activity of the solution changes so that solutions are obtained which have the same antimicrobial activity as taurolidin solutions. If 1 equivalent of taurinamide hydrochloride is used for adjusting the activity, the solutions obtained differ from those which were obtained by dissolving taurolidin through the presence of chloride.

At an appropriate ratio of taurinamide to methylene glycol of 2:1, the stoichiometry of the constituents of the mixture corresponds to the stoichiometry of the compound (V) which is likewise described in the abovementioned publication in Acta Cryst. (1999), C55, 232-234. It is to be assumed that aqueous solutions which are formed by dissolving said compound (V) likewise have antimicrobial activity which approximately reflects the number of methylene bridges between ring nitrogen atoms in (V). Aqueous solutions which are prepared by dissolving said compound (V) may be considered as aqueous solutions of cyclotaurolidine which were modified appropriately by taurinamide addition and are therefore likewise within the scope of the present invention.

An aqueous lock solution may further comprise constituents selected from the group consisting of taurinamide, taurinamide hydrochloride, one or more substances with antibiotic activity, physiologically tolerated polyol, polyvinylpyrrolidone, and at least one of buffer substances and heparin

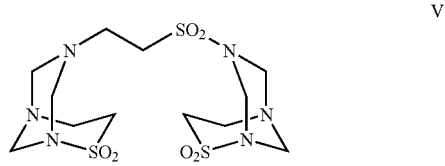

V

DETAILED DESCRIPTION OF PREFERRED EMBODIMENTS

Below, the present invention is explained in more detail with reference to examples which firstly describe a novel and advantageous process for the preparation of cyclotaurolidine and secondly give results which are obtained in the testing of the antimicrobial activity of aqueous solutions which were prepared from cyclotaurolidine.

EXAMPLES

1. Preparation of 7-oxa-2-thia-1,5-diazabicyclo[3.3.1]nonane-2,2-dione ("cyclotaurolidine") Starting from Taurinamide Hydrochloride Taurinamide hydrochloride (250.0 g, 1.55 mol; prepared according to EP 863 133 B1) was added to a solution of sodium hydroxide (60.0 g, 1.50 mol) in water (700 ml). A clear colorless solution was obtained, which was added dropwise within a period of 5 min to a stirred aqueous solution of formaldehyde (35%, 1000 ml). During the addition, the temperature of the clear colorless mixture increased from room temperature to 47° C. On heating the solution obtained to 62° C., the solution became turbid. It was stirred for a further 30 min at a temperature of about 45-47° C. and then cooled to 10° C. and stirred at this temperature for a further 20 min. The result was a colorless precipitate, which was separated from the aqueous phase with suction and which was washed with water and then ethanol and then dried. The yield was 224.8 g and the melting point of the crystalline product was 148.5° C.

Analysis:

Found: C, 33.79; H, 5.593; N, 15.68; S, 18.11.

Calculated (for $C_5H_{10}N_2O_3S$—molar mass 178.21 g): C, 33.69; H, 5.65; N, 15.71; S, 17.99.

IR: v $(cm^{-1})$=2872, 1384, 1329, 1269, 1225, 1185, 1138, 1064, 1014, 995, 973, 947, 874, 791, 743, 663, 615.

$^{13}$C NMR (CHCl$_3$): δ (ppm)=48.8, 51.5, 69.0, 79.2, 84.0.

The product is an odorless, crystalline powder which can be recrystallized from, for example, ethanol and purified and which was stable in the air at customary temperatures, can be easily handled and not only has the abovementioned solubility in water but is also soluble in various organic solvents. In contrast to taurolidin, cyclotaurolidine can therefore also be processed to give formulations in organic vehicles, for example in many customary organic vehicle materials for pharmaceutical and cosmetic purposes. This permits, for example, advantageous use in ointments and gels and on plastic surfaces (in the surface layers of stents), for example in agents for disinfecting the skin surface or as a fungicide, for example for the feet.

2. Preparation of Cyclotaurolidine Starting from Taurolidin

The reaction of taurolidin with an excess of methylene glycol (aqueous formaldehyde), mentioned in Acta Cryst. (1999), C55, 232-234, was carried out for control purposes. For this purpose, a total of 20 g of taurolidin were added in 10 portions to a stirred solution of formaldehyde (100 ml, 35%, EuAB 5.0) at room temperature. After the addition of the first three portions, the mixture was stirred until it became clear. Thereafter, the mixture was gradually heated to 55° C., and the remainder of the taurolidin was added (in 7 portions). The colorless solution obtained was stirred for 10 min, and the temperature was then slowly reduced to 5° C. by cooling. The solution became turbid at 30° C. After the solution had been stirred for 30 min at 5° C., the precipitate formed was filtered off with suction and washed with cold water. The yield of the moist crude material was 21 g. Drying and recrystallization from ethanol gave colorless crystals, which were isolated by filtration with suction.

Yield: 17 g; $R_f$=0.65 (CHCl$_3$/MeOH 9.1, silica gel); melting point 148-149° C. The elemental analysis and the IR and $^{13}$C-NMR data confirmed the identity of the product obtained starting from taurolidin with the product according to example 1.

3. Investigation of the Antimicrobial Activity of Aqueous Cyclotaurolidine Solutions Exploratory experiments for dissolving cyclotaurolidine in water showed that solubility of cyclotaurolidine in 100 ml of water at room temperature was not more than about 1.3 g.

For the test for antimicrobial activity, aqueous solutions containing 0.85 g of cyclotaurolidine in 100 ml of water were used.

With regard to a possible use as lock solution, a solution was prepared, for testing for antimicrobial activity, by dissolving 0.85 g of cyclotaurolidine and 4.8 g of monosodium citrate in water (100 ml) with stirring, a clear colorless solution being obtained. After the pH of the solution had been adjusted to 6.3, the solution was filtered and filled into ampoules.

The bactericidal and fungicidal activity of the solution was tested by a recognized test laboratory according to DIN EN 1040 and DIN EN 1275 (membrane filtration) against the test organisms *S. aureus* (ATCC 6538), *P. aeruginosa* (ATCC 15442), *S. epidermis* (ATCC 12288), *C. albicans* (ATCC 10231) and *A. niger* (ATCC 16404). The microbial count reductions observed for an action time of the test solution of 60 min and of 24 h at a test temperature of 20°±1° C. were determined.

The results are given in log steps of the microbial count reduction, minimum reductions of ≧5.0 log steps being required with respect to the test microorganisms *S. aureus*, *P. aeruginosa* and *S. epidermis* and log steps of ≧4.0 for *C. albicans* and *A. niger*, based on DIN EN 1040 and DIN EN 1275.

After 60 min, the following microbial count reductions (given in log steps) were obtained: *S. aureus* 2.04, *P. aeruginosa*>5.27, *S. epidermis* 1.22, *C. albicans*>4.26, *A. niger*>4.08.

After an action time of 24 h, the corresponding values were >5.25 for *S. aureus*,>5.27 for *P. aeruginosa*, >5.29 for *S. epidermis*, >4.26 for *C. albicans* and >4.08 for *A. niger*.

A comparative solution of the prior art in the form of an aqueous solution containing 2% by weight of taurolidin and a corresponding amount of citrate and having a pH of 6.3 gave the following corresponding results:

60 min: *S. aureus* 1.33, *P. aeruginosa*>5.27, *S. epidermis*>0.99, *C. albicans* 0, *A. niger* 1.18.

24 h: ≧5.25, ≧5.27, ≧5.29, 3.70, ≧4.08.

A comparison of the results shows that in spite of a concentration which is substantially below the customary taurolidin solutions, the solution prepared using cyclotaurolidine gave better microbial count reductions under all test conditions. Particularly striking is the considerably higher activity with respect to the problematic microorganisms *C. albicans* and *A. niger*, for which the required values are reached after only 60 min, whereas the known comparative solution reaches the required values for these eukaryotic microorganisms only after 24 h in the case of *A. niger*.

While the invention has been illustrated and described as embodied in the described antimicrobial formulation, it is not intended to be limited to the details shown since various modifications and changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed as new and desired to be protected by Letters Patent is set forth in the appended claims and their equivalents:

1. A method for the production of an antimicrobial formulation for use in a technical or medical application, comprising the steps of: dissolving or dispersing an antimicrobial amount of 7-oxa-2-thia-1,5-diazabicyclo[3.3.1]nonane-2,2-dione ("cyclotaurolidine") in an aqueous carrier for the antimicrobial formulation.

2. The method as claimed in claim 1, wherein the carrier is a gel.

3. The method as in claim 1, wherein the formulation is a watery solution of cyclotaurolidine in the range from 0.5% by weight to a concentration of saturation at room temperature and including at least one of: a solution of alkali citrate and citric acid.

4. An aqueous lock solution for catheters and port systems comprising cyclotaurolidin and monosodium citrate in watery solution, the lock solution having a pH in the range of from 4.5 to 7.5.

5. The lock solution of claim 4, wherein the pH is from 5.5 to 7.5.

6. The aqueous lock solution as claimed in claim 4, further comprising constituents selected from the group consisting of taurinamide, taurinamide hydrochloride, one or more substances with antibiotic activity, physiologically tolerated polyol, polyvinylpyrrolidone, and at least one of buffer substances and heparin.

7. A method for producing 7-oxa-2-thia-1,5-diazabicyclo[3.3.1]nonane-2,2-dione ("cyclotaurolidin") comprising the steps of adding a solution of 2-aminoethanesulfonylamide (taurinamide) to an aqueous solution of formaldehyde containing formaldehyde in at least 3 times the stoichiometric amount based on the amount of taurinamide to obtain a reaction solution; thereafter cooling the reaction solution to obtain a solid reaction product, filtering the solid reaction product off from the reaction solution and, optionally purifying the reaction product by recrystallization.

8. The method as claimed in claim 7, wherein the taurinamide solution has a concentration of more than 10% by weight in an aqueous solution added dropwise to an excess of an approximately 35% solution of formaldehyde in water to obtain the reaction solution, heating the solution to complete the reaction before cooling the solution to obtain a precipitate.

9. The method of claim 8, wherein the concentration of the taurinamide solution is at least 20% by weight.

10. The method as claimed in claim 8, further comprising the steps of heating the reaction mixture to a temperature of at least 55° C. after adding the taurinamide and stirring the mixture in a heated state from 10 min to 45 min and then cooling the mixture to a temperature of less than 15° C. to obtain the precipitate.

11. The process as claimed in claim 10, wherein heating is to at least 60° C. and cooling is to a temperature to about 10° C.

12. The method according to claim 1, further comprising adding monosodium citrate in watery solution and adjusting the antimicrobial formulation to a pH in the range of from 4.5 to 7.5 to obtain a lock solution for catheters and port systems.

13. The method of claim 12, wherein the pH is from 5.5 to 7.5.

14. The method as claimed in claim 12, further comprising constituents selected from the group consisting of taurinamide, taurinamide hydrochloride, one or more substances with antibiotic activity, physiologically tolerated polyol, polyvinylpyrrolidone, and at least one of buffer substances and heparin.

* * * * *